United States Patent
Funk

(10) Patent No.: US 12,032,342 B2
(45) Date of Patent: Jul. 9, 2024

(54) PERSONALIZED CONTROL OF AN OUTDOOR POWER EQUIPMENT TOOL

(71) Applicant: HUSQVARNA AB, Huskvarna (SE)

(72) Inventor: Jon Funk, Concord, NC (US)

(73) Assignee: HUSQVARNA AB, Huskvarna (SE)

(*) Notice: Subject to any disclaimer, the term of this patent is extended or adjusted under 35 U.S.C. 154(b) by 484 days.

(21) Appl. No.: 17/285,954

(22) PCT Filed: Oct. 19, 2018

(86) PCT No.: PCT/IB2018/058163
§ 371 (c)(1),
(2) Date: Apr. 16, 2021

(87) PCT Pub. No.: WO2020/079480
PCT Pub. Date: Apr. 23, 2020

(65) Prior Publication Data
US 2021/0389735 A1 Dec. 16, 2021

(51) Int. Cl.
*G08B 21/02* (2006.01)
*A61B 5/00* (2006.01)
(Continued)

(52) U.S. Cl.
CPC .............. *G05B 13/024* (2013.01); *A61B 5/01* (2013.01); *A61B 5/021* (2013.01); *A61B 5/024* (2013.01);
(Continued)

(58) Field of Classification Search
None
See application file for complete search history.

(56) References Cited

U.S. PATENT DOCUMENTS 5,314,389 A * 5/1994 Dotan .................... A63B 69/00
482/3
5,893,817 A * 4/1999 Morgan ............... A01D 34/001
482/902
(Continued)

FOREIGN PATENT DOCUMENTS

CN 107065796 A 8/2017
CN 108040578 A 5/2018
(Continued)

OTHER PUBLICATIONS

International Search Report and Written Opinion in the International Application No. PCT/IB2018/058163 dated Jul. 1, 2019.

*Primary Examiner* — Jonathan M Dager
(74) *Attorney, Agent, or Firm* — BURR & FORMAN LLP

(57) ABSTRACT

A controller for an outdoor power equipment tool may include processing circuitry operably coupled to a sensor network of the outdoor power equipment tool and in data communication with a network. The processing circuitry may be configured to receive fitness data of a user from a fitness device via the network. The processing circuitry may be further configured to receive sensor data from the sensor network. The processing circuitry may be even further configured to compare the fitness data to the sensor data, and in response to the comparison of the fitness data to the sensor data, cause an adjustment to the operational parameters of the outdoor power equipment tool.

16 Claims, 7 Drawing Sheets

(51) Int. Cl.
  *A61B 5/01*    (2006.01)
  *A61B 5/021*   (2006.01)
  *A61B 5/024*   (2006.01)
  *A61B 5/145*   (2006.01)
  *G05B 13/02*   (2006.01)

(52) U.S. Cl.
  CPC ...... *A61B 5/14532* (2013.01); *A61B 5/14542* (2013.01); *A61B 5/4266* (2013.01); *A61B 5/4866* (2013.01)

(56) References Cited

U.S. PATENT DOCUMENTS

| | | | |
|---|---|---|---|
| 8,938,261 | B2 | 1/2015 | Lee et al. |
| 9,319,860 | B2 | 4/2016 | Tanaka et al. |
| 9,973,831 | B2* | 5/2018 | Mejegård ................ H04W 4/80 |
| 10,032,123 | B2* | 7/2018 | Mejegård ................ G06Q 10/06 |
| 11,055,979 | B1* | 7/2021 | Hitt ........................ H04B 1/385 |
| 11,297,766 | B1* | 4/2022 | Wynn-Grayson ...... A01D 34/90 |
| 11,701,063 | B2* | 7/2023 | Hitt ...................... A61B 5/7275 |
| | | | 600/301 |
| 2007/0037668 | A1* | 2/2007 | Cofrin ................. A63B 21/4017 |
| | | | 482/51 |
| 2014/0303899 | A1* | 10/2014 | Fung ....................... B60R 99/00 |
| | | | 702/19 |
| 2015/0105687 | A1* | 4/2015 | Abreu ..................... A61B 5/01 |
| | | | 600/549 |
| 2015/0123815 | A1* | 5/2015 | Mejegård ............... G06Q 10/06 |
| | | | 340/870.07 |
| 2018/0126248 | A1* | 5/2018 | Dion .......................... A63B 1/00 |
| 2018/0263182 | A1* | 9/2018 | Albinger ................ G06F 21/36 |
| 2019/0077003 | A1* | 3/2019 | Lennings ............... G05B 19/05 |
| 2020/0245938 | A1* | 8/2020 | Xu .......................... G16H 10/60 |
| 2021/0052221 | A1* | 2/2021 | Panneer Selvam ... A61B 5/1117 |
| 2021/0153754 | A1* | 5/2021 | Ozawa .................. B60N 2/002 |
| 2021/0169417 | A1* | 6/2021 | Burton .................. A61B 5/4857 |
| 2021/0213956 | A1* | 7/2021 | Schön .................... B60W 40/08 |
| 2021/0299518 | A1* | 9/2021 | Brammer ........... A63B 24/0062 |
| 2022/0176829 | A1* | 6/2022 | Haugen .................. B60L 3/106 |
| 2023/0172101 | A1* | 6/2023 | Lardieri .................. A01D 34/006 |
| | | | 56/10.8 |

FOREIGN PATENT DOCUMENTS

| | | | | |
|---|---|---|---|---|
| DE | 202006008176 U1 | | 8/2006 | |
| JP | H0521938 U | | 3/1993 | |
| WO | WO-2014120893 A1 * | | 8/2014 | ........... A01D 34/008 |
| WO | 2017151045 A1 | | 9/2017 | |
| WO | WO-2017151045 A1 * | | 9/2017 | ............... B25F 5/00 |

* cited by examiner

PERSONALIZED CONTROL OF AN OUTDOOR POWER EQUIPMENT TOOL

TECHNICAL FIELD

Example embodiments generally relate to an outdoor power equipment tool and, more particularly, to facilitating personalized control of the device by a user based on health or fitness data or metrics received from a fitness device of the user.

BACKGROUND

Lawn care tasks may be performed using various devices or tools configured for the performance of corresponding specific tasks. For example, certain tasks, like grass cutting, are typically performed by lawn mowers. Regardless of the outdoor power equipment device or tool and the specific task they are configured to perform, a user of the outdoor power equipment device or tool, in particular walk-behind devices or tools, may desire to have more control over the specific settings and operation of the tool. In this regard, the user may wish to have more personalized and tailored settings when operating the tool. For instance, the user may wish to have settings tailored to their specific health or fitness metrics. Thus, for example, rather than having generic drive speed control settings on the tool, a user may wish to have a drive speed setting that corresponds to the user's normal walking speed.

BRIEF SUMMARY OF SOME EXAMPLES

Accordingly, in order to facilitate a tailored and personalized operation of an outdoor power equipment tool by a user, some example embodiments may provide a tool that is configured to receive health or fitness data or metrics from a fitness device of a user. The health or fitness data or metrics received by the tool may be used in adjusting settings of the tool to correspond to the user and therefore optimize operation of the tool while ensuring the optimal safety and health of the user.

In one example embodiment, a controller for an outdoor power equipment tool may be provided. The controller may include processing circuitry operably coupled to a sensor network of the outdoor power equipment tool and in data communication with a network. The processing circuitry may be configured to receive fitness data of a user from a fitness device via the network. The processing circuitry may be further configured to receive sensor data from the sensor network, the sensor data corresponding to operational parameters of the outdoor power equipment tool. The processing circuitry may be even further configured to compare the fitness data to the sensor data, and in response to the comparison of the fitness data to the sensor data, cause an adjustment to the operational parameters of the outdoor power equipment tool.

In a further example embodiment, a method for adjusting operational parameters of an outdoor power equipment tool may be provided. The method may include receiving fitness data of a user from a fitness device via a network. The method may further include receiving sensor data from a sensor network of the outdoor power equipment tool, the sensor data corresponding to operational parameters of the outdoor power equipment tool. The method may even further include comparing the fitness data to the sensor data, and in response to the comparison of the fitness data to the sensor data, causing an adjustment to the operational parameters of the outdoor power equipment tool.

In an even further example embodiment, a system may be provided. The system may include an outdoor power equipment tool and a fitness device. The outdoor power equipment tool may include a sensor network and controller. The controller may include processing circuitry operably coupled to the sensor network of the outdoor power equipment tool and in data communication with a network. The processing circuitry may be configured to receive fitness data of a user from the fitness device via the network. The processing circuitry may be further configured to receive sensor data from the sensor network, the sensor data corresponding to operational parameters of the outdoor power equipment tool. The processing circuitry may be even further configured to compare the fitness data to the sensor data, and in response to the comparison of the fitness data to the sensor data, cause an adjustment to the operational parameters of the outdoor power equipment tool.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

Figure 1:
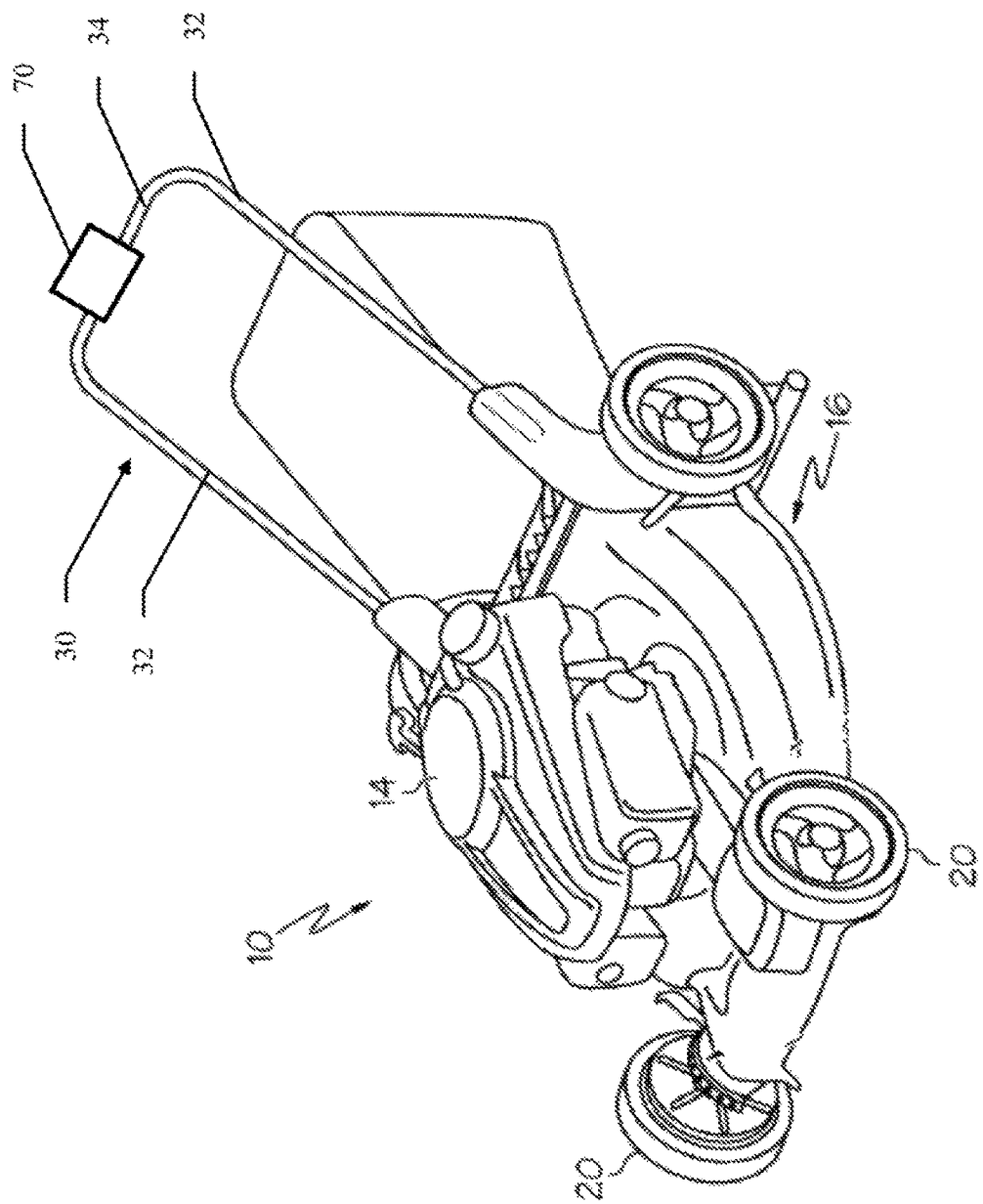
FIG. 1 illustrates a walk behind lawn care device according to an example embodiment.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout. Furthermore, as used herein, the term "or" is to be interpreted as a logical operator that results in true whenever one or more of its operands are true. As used herein, operable coupling should be understood to relate to direct or indirect connection that, in either case, enables functional interconnection of components that are operably coupled to each other.

Example embodiments herein may improve and simplify the ability of a user of an outdoor power equipment tool (tool) to personalize or tailor operation of the tool in manner that corresponds to a detected overall health or fitness of the user. Accordingly, in order to facilitate personalized control over the tool, the tool may be configured to receive health or fitness data (fitness data) or metrics from a fitness device of the user. The fitness data or metrics received by the tool may ensure that operation of the tool corresponds to the fitness ability of the user.

FIG. 1 illustrates a walk behind lawn care tool 10 (i.e., the device) according to an example embodiment. However, it should be appreciated that example embodiments may also be practiced in connection with any other lawn care tool or outdoor power equipment tool that may benefit from connectivity with a fitness device, as discussed herein. For example, the outdoor power equipment tool could alternatively be a blower, a chainsaw, a trimmer, an edger, a snow removal device, a tiller, or the like.

As shown in FIG. 1, the tool 10 may include a power source 14 and a blade housing 16. The blade housing 16 may be configured to house a rotatable cutting blade (not shown). The rotatable cutting blade may be a working assembly of the tool 10. In other example embodiments, for example, if the tool 10 is a chainsaw, the working assembly may be a chain, or in cases of where the tool 10 is a blower, the working assembly may be a fan.

The cutting blade of the tool 10 may be suspended above the ground by a rotatable shaft (also not shown) of the tool 10 that may be rotated responsive to operation of the power source 14 of the tool 10. In some cases, the power source 14 may be an engine that is battery-powered. It should be understood, however, that the power source 14 may alternatively be an electric or gasoline-powered engine or the like.

As further shown in FIG. 1, the tool 10 may include a mobility assembly 20 on which a substantial portion of the weight of the tool 10 may rest when the tool 10 is stationary. In some cases, the mobility assembly 20 may be operably coupled to the blade housing 16. In some cases, the mobility assembly 20 may include front wheels and back wheels. The mobility assembly 20 may also provide for movement of the tool 10. In some cases, the mobility assembly 20 may be driven via power from the power source 14 that may be selectively provided to either or both of the front and back wheels of the mobility assembly 20. However, in some cases, the mobility assembly 20 may simply provide for mobility of the tool 10 responsive to pushing by a user of the tool 10 if, for example, drive power is not being provided to both the front and back wheels of the mobility assembly 20. In other words, for example, the mobility assembly 20 may be an active or passive provider of mobility for the tool 10.

In accordance with an example embodiment, the tool 10 may further include a handle assembly 30. The handle assembly 30 may include two handle members 32 that extend generally rearward and upward from opposing sides of a rear portion of the blade housing 16. The handle members 32 may be substantially parallel to each other and may be connected to each other at their distal ends via a cross bar 34. The handle members 32 may be adjustable in length or may be foldable to reduce the amount of space that the tool 10 consumes when stored or shipped.

Figure 2:
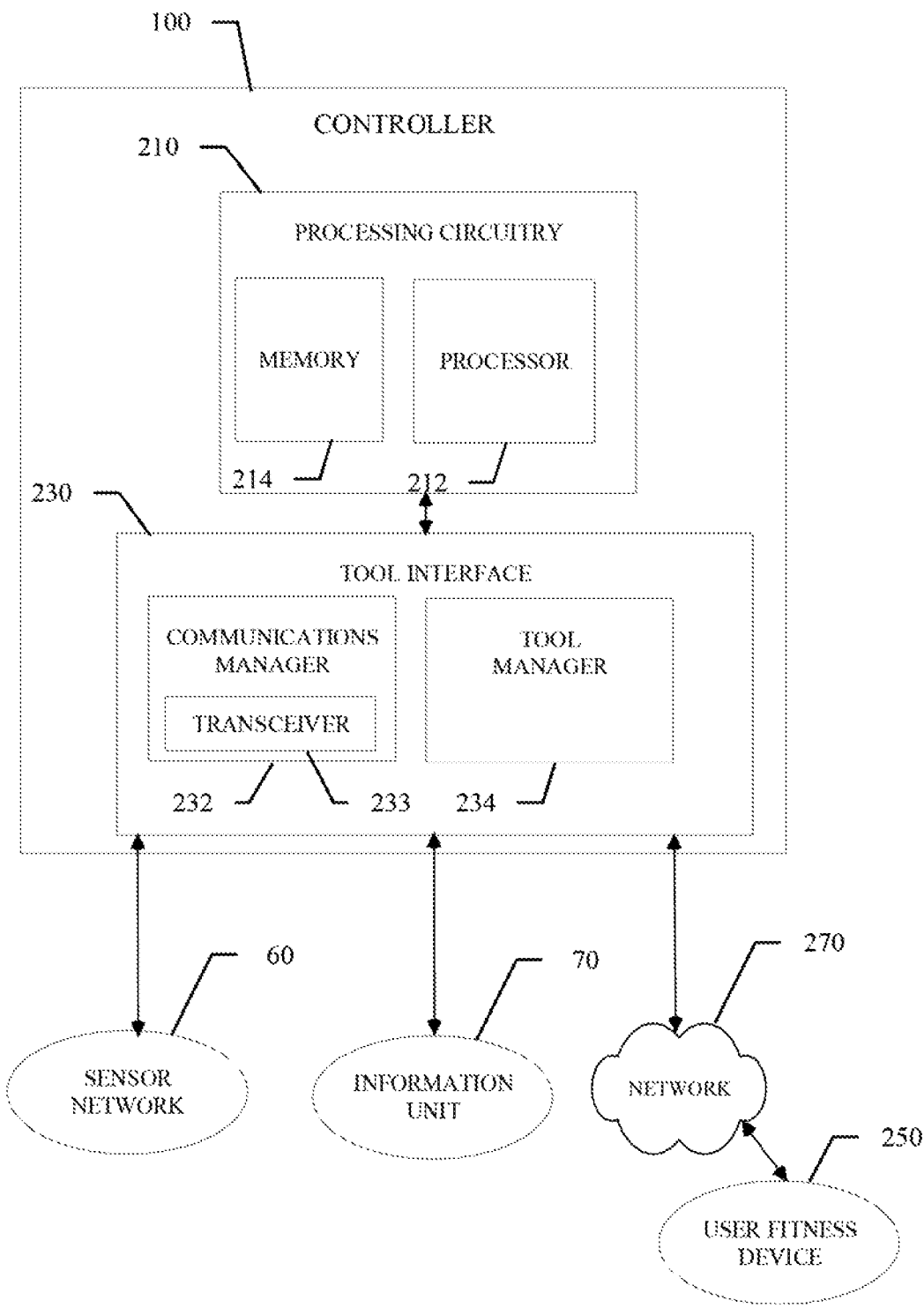
FIG. 2 illustrates a block diagram of various components of a controller of a walk behind lawn care device according to an example embodiment.

In some cases, the tool 10 may also include a sensor network 60 (see FIG. 2). The sensor network 60 may be configured to detect various operating parameters associated with the operation of the tool 10. The sensor network 60 may include one or more sensors disposed in various locations on the tool 10. For example, a sensor disposed at or proximate the power source 14 may be configured to determine engine parameters such as RPM or temperature. Moreover, a sensor disposed at or proximate the mobility assembly 20 may be configured to detect or determine an operating speed of the tool 10, the operating speed being the speed of the tool 10 over the ground (e.g., how fast the mower is moving or driving forward or the like). Additionally, a sensor disposed at or proximate the cutting blade may be configured to determine blade speed. In some embodiments, one or more sensors may determine battery status, energy efficiency, device speed, blade speed, blade height, or the like. Furthermore, one or more of the sensors of the sensor network 60 may be configured to determine engine run time, device work time, and other operational parameters.

The tool 10 of FIG. 1 may include gauges, displays, or other components that indicate or display information to the user of the tool 10 regarding the operational parameters related to the operation or usage of the tool 10 (e.g., the parameters received from the sensor network 60). The gauges, displays, or other user interface components may be disposed on an information unit 70 of the tool 10. The information unit 70 may be operably coupled to and detachable from a portion of the tool 10. For example, the information unit 70 may be located at or proximate the handle assembly 30. The user may manually control operation of the tool 10 or provide instructions to the tool 10 through the information unit 70. In this regard, the information unit 70 may have a touch screen, function buttons, etc. that allow for user interaction. In some cases, the information unit 70 may actually be a mobile phone, computing device, or the like of the user.

Furthermore, the tool 10 may include a controller 100 (see FIG. 2) that is configured to facilitate communication between components (e.g., the sensor network 60) of the tool 10 and external devices (e.g., user fitness device 250 (see FIG. 2), computing devices, etc.) for the transfer of certain types of user fitness data, tool data, or the like. The user fitness device 250, as used herein, may be a fitness tracker located on a mobile phone or a computing device of the user. In other cases, however, the user fitness device 250 may be a computing device or mobile phone that has received health or fitness information from the user from an external fitness tracker (e.g., stand along fitness devices worn on wrist or the like).

To facilitate interaction between the tool 10 and the user fitness device 250, the controller 100 may include circuitry that enables communication directly or indirectly between the tool 10 and the user fitness device 250. In this regard, the controller 100 allows for information gathered from the user fitness device 250 to be transferred to the tool 10 for adjustment of settings of the tool 10 to thereby enabling optimum performance of the tool 10 that is tailored to the user of the tool 10. Furthermore, the controller 100 may cause the information unit 70 to display certain user fitness data, tool data, or the like such that the user may have full access to the data being received or the operational settings of the tool 10 and may change them as desired.

As will be further described below, the controller 100 may be configured to interact with and gather certain operational parameters (e.g., battery status, energy efficiency, device speed, blade speed, blade height, or the like) about the tool 10 via the sensor network 60. The controller 100 may be further configured to compare these operational data or parameters of the tool 10 to the data received from the user fitness device 250 (e.g., average walking speed, heart rate, blood pressure, sweat volume, temperature, blood glucose levels, calories burned, UV exposure, oxygen content, or the like). In this regard, for example, the controller 100 may be configured to compare a detected tool speed to a received average walking speed of the user. In some cases, the comparison may include comparing the run time of the tool 10 to calories burned, UV exposure, sweat volume, or temperature of the user.

Based on the comparison, the controller 100 may be then configured to change certain settings of the tool 10 such that the settings of the tool 10 correspond to the fitness data of the user received from the user fitness device 250 or to ensure the well-being of the user. Using the examples above, the controller 100 may receive the average walking speed of the user from the user fitness device 250, and if necessary, the controller 100 may change a drive speed of the tool 10 to correspond to the user's average walking speed. Furthermore, the controller 100 may receive the run time of the device and recommend or cause a shutdown of the device. In this regard, the controller 100 may have certain stored preset health limits or thresholds that a user's fitness data may be compared to (e.g., recommended sun exposure, sweat volume, body temperature, etc.). Accordingly, in order to enable personalized operation of the tool 10, the controller 100 may be configured to extract information from the sensor network 60 about the operation of the tool 10 (i.e., operational parameters) and cause the sensor network 60 to change certain settings of the tool 10 to correspond to the user. Furthermore, the controller 100 may be configured to cause the information unit 70 to display the fitness data received from the user fitness device 250 (e.g., heart rate, walking speed, blood pressure, etc.) and certain operational parameters of the tool 10 (e.g., tool speed, battery status, etc.).

FIG. 2 illustrates a block diagram of the controller 100 of the tool 10 according to an example embodiment. As shown in FIG. 2, the controller 100 may include or otherwise be in communication with processing circuitry 210 that is configurable to perform actions in accordance with example embodiments described herein. In this regard, for example, the controller 100 may utilize the processing circuitry 210 to provide data generated by the sensor network 60 of the tool 10 regarding various indications of device activity (e.g., operational parameters or location information). In some cases, the processing circuitry 210 may be configured to perform data processing, control function execution or other processing and management services according to an example embodiment. However, in other examples, the processing circuitry 210 may be configured to manage extraction, storage or communication of data received at the processing circuitry 210. As such, for example, the functions attributable to the controller 100 may be carried out by the processing circuitry 210.

The processing circuitry 210 may be configured to perform data processing, control function execution, or other processing and management services according to an example embodiment of the present invention. In some embodiments, the processing circuitry 210 may be embodied as a chip or chip set. In other words, the processing circuitry 210 may comprise one or more physical packages (e.g., chips) including materials, components, or wires on a structural assembly (e.g., a baseboard). The structural assembly may provide physical strength, conservation of size, or limitation of electrical interaction for component circuitry included thereon. The processing circuitry 210 may therefore, in some cases, be configured to implement an embodiment of the present invention on a single chip or as a single "system on a chip." As such, in some cases, a chip or chipset may constitute means for performing one or more operations for providing the functionalities described herein.

In an example embodiment, the processing circuitry 210 may include a processor 212 and memory 214 that may be in communication with or otherwise control a tool interface 230. As such, the processing circuitry 210 may be embodied as a circuit chip (e.g., an integrated circuit chip) configured (e.g., with hardware, software or a combination of hardware and software) to perform operations described herein. However, in some embodiments, the processing circuitry 210 may be embodied as a portion of an on-board computer housed in the tool 10 with a tool manager 234 or communications manager 232 to control operation of the tool 10 relative to its interaction with other devices.

The tool manager 234 and the communications manager 232 of the controller 100 may be embodied as or otherwise controlled by the processing circuitry 210. However, in some cases, the processing circuitry 210 may be associated with only a specific one of the tool manager 234 or the communications manager 232, and a separate instance of processing circuitry may be associated with the other. Yet in some cases, the processing circuitry 210 could be shared between the tool manager 234 and the communications manager 232 or the processing circuitry 210 could be configured to instantiate both such entities. Thus, although FIG. 2 illustrates such an instance of sharing the processing circuitry 210 between the tool manager 234 and the communications manager 232, it should be appreciated that FIG. 2 is not limiting in that regard.

Each of the tool manager 234 and the communications manager 232 may employ or utilize components or circuitry that acts as a tool interface 230. The tool interface 230 may include one or more interface mechanisms for enabling communication with other devices (e.g., the tool 10 (via the sensor network 60) and associated information unit 70 or the user fitness device 250 (via a network 270)). In some cases, the tool interface 230 may be any means such as a device or circuitry embodied in either hardware, or a combination of hardware and software that may be configured to receive or transmit data from/to components in communication with the processing circuitry 210 via internal communication systems of the controller 100. With respect to the communications manager 232, the tool interface 230 may further include wireless communication equipment (e.g., a one way or two way radio) for at least receiving information from the user fitness device 250 via the network 270. As such, the tool interface 230 of the communications manager 232 may include an antenna and radio equipment for conducting Bluetooth, WiFi, or other short range communication, or for employing other longer range wireless communication protocols for communicating with the user fitness device 250 (via the network 270) instances associated with access to a wide area network. The network 270, in some cases, may be representative of a direct connection between the controller 100 and the sensor network 60, user fitness 250, information unit 70, or the like.

The processor 212 may be embodied in a number of different ways. For example, the processor 212 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processor 212 may be configured to execute instructions stored in the memory 214 or otherwise accessible to the processor 212. As such, whether configured by hardware or by a combination of hardware and software, the processor 212 may represent an entity (e.g., physically embodied in circuitry in the form of processing circuitry 210) capable of performing operations according to embodiments of the present invention while configured accordingly. Thus, for example, when the processor 212 is embodied as an ASIC, FPGA or the like, the processor 212 may be specifically configured hardware for conducting the operations described herein. Alternatively, as another example, when the processor 212 is embodied as an executor of software instructions, the instructions may specifically configure the processor 212 to perform the operations described herein.

In an example embodiment, the processor 212 (or the processing circuitry 210) may be embodied as, include or otherwise control the operation of the controller 100 based on inputs received by the processing circuitry 210. As such, in some embodiments, the processor 212 (or the processing circuitry 210) may be said to cause each of the operations described in connection with the controller 100 relative to undertaking the corresponding functionalities associated therewith responsive to execution of instructions or algorithms configuring the processor 212 (or processing circuitry 210) accordingly.

In an example embodiment, the memory 214 may include one or more non-transitory memory devices such as, for example, volatile and/or non-volatile memory that may be either fixed or removable. The memory 214 may be configured to store information, data, applications, instructions or the like for enabling the processing circuitry 210 to carry out various functions in accordance with example embodiments. For example, the memory 214 could be configured to buffer input data for processing by the processor 212. Additionally or alternatively, the memory 214 could be configured to store instructions for execution by the processor 212. As yet another alternative or additional capability, the memory 214 may include one or more databases that may store a variety of data sets responsive to input from the tool 10 or the user fitness device 250, or any other functional units or devices from which the controller 100 has previously extracted data. Among the contents of the memory 214, applications may be stored for execution by the processor 212 in order to carry out the functionality associated with each respective application. In some cases, the applications may include instructions for recognition of certain user fitness data and for initiation of one or more responses to the recognition of the data as described herein.

In some embodiments, the tool manager 234 may be any means such as a device or circuitry embodied in either hardware, or a combination of hardware and software that may be configured to receive or transmit data (e.g., operational parameters of the tool 10, fitness data of the user fitness device 250) to/from the tool 10. The tool manager 234 may also control or provide electrical connections or interfaces between the controller 100 and the tool 10 to monitor the sensor network 60 and enable the tool manager 234 to implement operational, safeguard, or protective functions as appropriate. These functions may be implemented based upon examination of the tool data and comparison of such data to various predefined thresholds or limits received from the user fitness device 250. In this regard, the tool manager 234 may receive the tool data (e.g., operational parameters) from the sensor network 60 and control the storage of the tool data (e.g., operational parameters) extracted from the sensor network 60 in order for comparison with any fitness data received from the user fitness device 250.

In an example embodiment, the communications manager 232 may be any means such as a device or circuitry embodied in either hardware, or a combination of hardware and software that is configured to receive or transmit tool data from/to the tool 10. In this regard, the communication manager 232 may include a transceiver 233 to facilitate communication between the controller 100 and any network devices (via the network 270). The network devices being, for example, the user fitness device 250. The communication manager 232 may therefore receive fitness data of the user via the network 270. This fitness data may include average walking speed, heart rate, blood pressure, sweat volume, temperature, blood glucose levels, calories burned, UV exposure, oxygen content, or the like. The fitness data may be stored in association with a user based on a specific user identifier or a user profile. However, it should also be understood that the controller 100 may be configured to intuitively determine the user based on the fitness data received without any explicit knowledge of the identity of the user (e.g., a first user has a first average walking speed and a second user has a second average walking speed). In other words, the controller 100 may be configured to determine the identity of the user based on recognizable patterns from fitness data received.

Furthermore, the fitness data may also be stored in association with temporal information that may indicate the time (or time period) that the metrics were obtained by the user fitness device 250 or the time that the metrics were transmitted from the user fitness device 250. The fitness data may be retrieved by or sent to the controller 100 at regular intervals or continuously, for example, during operation of the tool 10. In this regard, the controller 100 may be configured to start receiving data from the user fitness device 250 in response to a power on condition of the tool 10, and this data may be received continuously, at regular interval, or at predefined times in order to intuitively adjust the operational parameters of the tool 10. In some cases, the data from the user fitness device 250 may be received even when the tool 10 is not operational. For example, the tool 10 may periodically (e.g., nightly) receive the data when non-operational in order to ensure the tool 10 is started with settings specifically tailored for the user.

Figure 3:
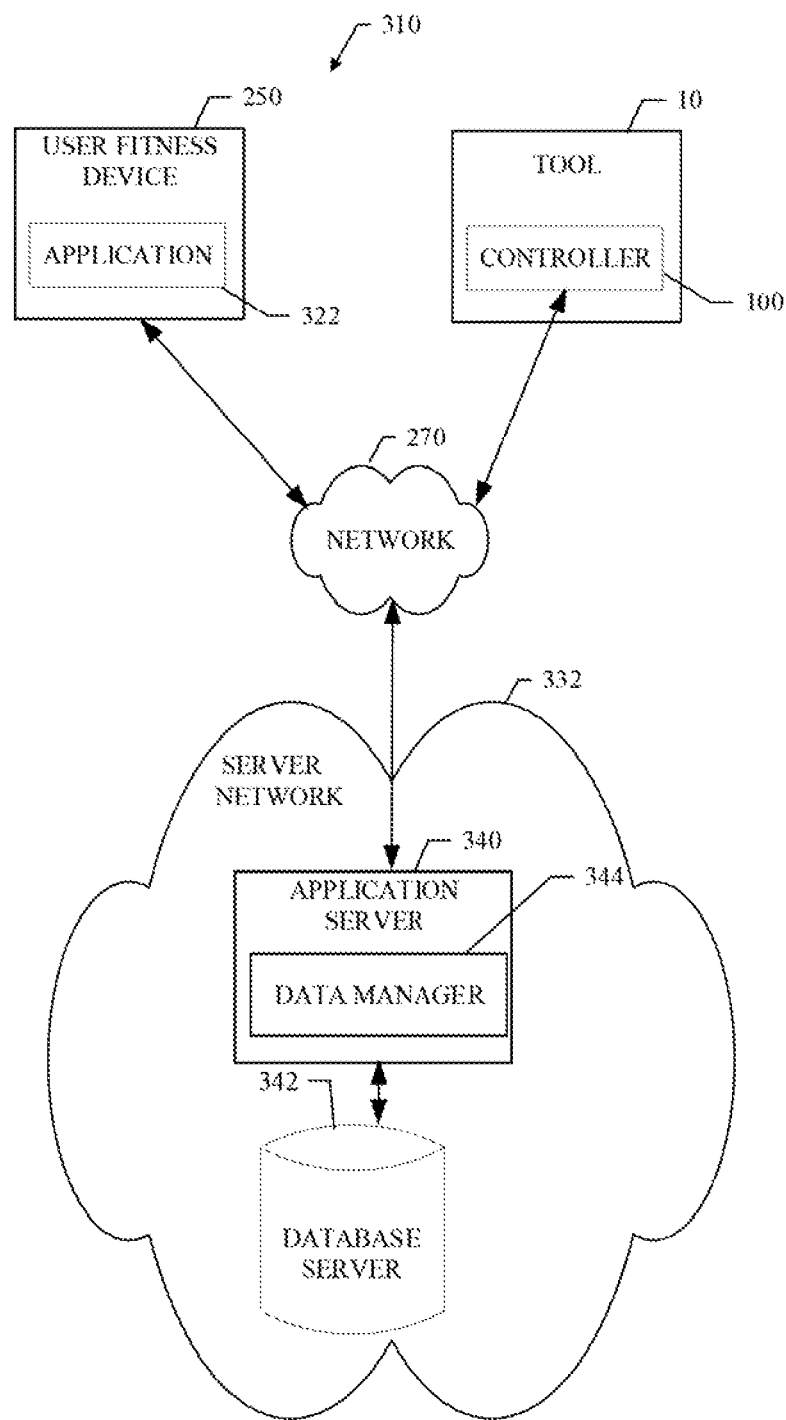
FIG. 3 illustrates a block diagram of a system that may be used in connection with causing an image recognition query according to an example embodiment.

FIG. 3 illustrates a diagrammatic representation of a system 310 in accordance with an example embodiment described herein. As discussed above, the controller 100 may be configured to receive and manage the operational parameters received from the sensor network 60 and the user fitness device 250 received over the network 270. However, in some example embodiments, components of server network 332 in the system 310 may execute applications for storage or analysis of the fitness data, and in some cases, the operational parameters detected by sensor network 60. In this regard, one or more application servers (e.g., application server 340), or a database server 342, together may form respective elements of a server network 332. Although the application server 340 and the database server 342 are each referred to as "servers," this does not necessarily imply that they are embodied on separate servers or devices. As such, for example, a single server or device may include both entities and the database server 342 could merely be represented by a database or group of databases physically located on the same server or device as the application server 340. The application server 340 and the database server 342 may each include hardware or software for configuring the application server 340 and the database server 342, respectively, to perform various functions. As such, for example, the application server 340 may include processing logic and memory enabling the application server 340 to access or execute stored computer readable instructions for performing various functions. In an example embodiment, one function that may be provided by the application server 340 may be the provision of access to information or services related to the fitness data of the user. For example, the application server 340 may be configured to receive the data transmitted by the user fitness device 250 and the tool 10 via the network 270. The application server 340 may then be configured to analyze the fitness data of the user relative to the sensor data to determine if changes are needed to the operational settings of the tool 10 to facilitate operation of the tool 10 that is tailored for the specific user. Furthermore, the application server 340 may be configured to communicate the data received from the tool 10 or the user fitness device 250 to the tool 10 via the network 270 for display on the information unit 70.

In some embodiments, for example, the application server 340 may therefore include an instance of a data manager 344 comprising stored instructions for handling activities associated with practicing example embodiments as described herein. As such, in some embodiments, the user fitness device 250 (e.g., the user's mobile phone) may access the data manager 344 online via an application 322 and utilize the services provided thereby. However, it should be appreciated that in other embodiments, the data manager 344 may be initiated from an integrated memory of the user fitness device 250. It should be understood that the user fitness device 250 may be a fitness tracker located on a mobile phone or computing device of the user, for example. In other cases, however, the user fitness device 250 may be a computing device or mobile phone that has received health or fitness information from the user from an external fitness tracker (e.g., stand along fitness devices worn on wrist or the like).

In some example embodiments, the data manager 344 may be provided from the application server 340 (e.g., via download over the network 270) to the data manager 344 to enable the user fitness device 250 to instantiate an instance of the data manager 344 for local operation. As yet another example, the data manager 344 may be instantiated at the user fitness device 250 responsive to downloading instructions from a removable or transferable memory device carrying instructions for instantiating the data manager 344 at the user fitness device 250. In such an example, the network 170 may, for example, be a peer-to-peer (P2P) network where the data manager 344 includes an instance of the data manager 344 to enable another data manager 344 to act as a server to the user fitness device 250. In a further example embodiment, the data manager 344 may be distributed amongst the user fitness device 250 and the application server 340.

In an example embodiment, the application server 340 may include or have access to memory (e.g., internal memory or the database server 342) for storing instructions or applications for the performance of various functions and a corresponding processor for executing stored instructions or applications. For example, the memory may store an instance of the data manager 344 configured to operate in accordance with an example embodiment. In this regard, for example, the data manager 344 may include software for enabling the application server 340 to communicate with the network 270 or the user fitness device 250 for the provision or receipt of information associated with performing activities as described herein. Moreover, in some embodiments, the application server 340 may include or otherwise be in communication with an access terminal (e.g., a computer including a user interface) via which analysts may interact with, configure or otherwise maintain the system 100.

Furthermore, it should be understood that that applications executable at the application server 340 may include an application for reviewing, monitoring, or analyzing the data received from the tool 10 or the user fitness device 250. In some cases, the applications at the application server 340 may include an application for cloud management of the data received from the tool 10 or the user fitness device 250. Thus, for example, adaptive device settings, instructions or the like calculated or received from the data received may be used to specifically configure the device under identified circumstances or scenarios to maximize personalization of, for example, the tool 10 or, in some cases, a fleet of tools 10. In some example embodiments, either the application server 340 or the controller 100 may store configuration information specific to the tool 10 based on the fitness data of the user.

Accordingly, the controller 100 or the application server 340 or combination thereof may perform analysis of the operational parameters of the tool 10 and the fitness data of the user and generate alerts, configuration information, or the like that is specific to the tool 10. Thus, the data (device or fitness data) may be used for configuring the tool 10 accordingly, analyzing for trends, or other specific issues and then transmitted to the tool 10, and individual users or organizations can receive information specific to their tool 10. However, it should be understood that the information specific to the tool 10 may be benchmarked against the performance of other tools not associated with the individual users or organizations. This may be useful in determining the settings that correspond to optimal performance of the tool 10 and recommending the same to the user. Thus, the individual users or organizations can determine how hard they run their equipment or tools, or how well their battery or tool performs relative to all other tools monitored by the server network 332. Accordingly, it should be understood that the server network 332 may be used to monitor or receive data from several tools not necessarily owned or operated by the same organization or user (e.g., tools specific to a particular manufacturer or retailer).

Furthermore, as shown in FIG. 3, the user fitness device 250 (e.g., a mobile or computing device of the user) may include an application 322 that may be configured to transmit the user fitness data to the application server 340 or the controller 100. In some example embodiments, the user, instead of or in addition to receiving information at the information unit 70 of the tool 10, may receive or have access to the data via the application 322. In this regard, the application 322 may allow the user to review the tool data and the fitness data and corresponding operating conditions of the tool 10. It should be understood that the user device 250 may include (or otherwise have access to) memory for storing instructions or applications for the performance of various functions and a corresponding processor for executing stored instructions or applications. The user fitness device 250 may also include software or corresponding hardware for enabling the performance of the respective functions of the user device 250 as described herein. In this regard, the application 322 may include software for enabling the user fitness device 250 to communicate with the network 270 for requesting or receiving information or data via the network 270. The information or data receivable at the application 322 may include deliverable components (e.g., downloadable software to configure the user fitness device 250, or information for consumption/processing at the application 322). As such, for example, the application 322 may include corresponding executable instructions for configuring the user fitness device 250 to provide corresponding functionalities for enabling the user fitness device 250 to communicate with the network 170 or to the user the data received from the user fitness device 250 or the tool 10.

Thus, in accordance with example embodiments herein, the controller 100 (or in some cases the application server 340) may receive the operational parameters (i.e., the tool data) from the sensor network 60 of the tool 10 and the fitness data from the user fitness device 250. The fitness data may be analyzed in comparison to the sensor network data or other preset health or fitness thresholds or limits to determine if any adjustments are needed to various operating parameters of the tool 10 in order to provide a personalized and tailored operation of the tool 10 for the user. For example, at a general level, the controller 100 may receive information related to a drive speed of the tool 10 from the sensor network 60 and information related to a historical average walking speed of the user from the user fitness device 250—the historical average walking speed being based on a user fitness profile or previous data received from the user fitness device 250. If the historical average walking speed is greater than the drive speed of the tool 10, the controller 100 may be configured to cause the sensor network 60 to adjust the drive speed to an increased level to match the average walking speed of the user. If the historical average walking speed is less than the drive speed of the tool 10, the controller 100 may be configured to cause the sensor network 60 to adjust the drive speed to a decreased level to match the average walking speed of the user. In cases where the historical average walking speed of the user is substantially the same as the drive speed, the controller 100 will not cause the sensor network 60 to adjust the drive speed of the tool 10. For example, the controller 100 may receive data from the user fitness device 250 that the historical average walking speed of the user is 3 mph in normal conditions. Thus, in cases where the tool 10 is a walk-behind lawn mower (i.e., a tool used in normal ground conditions), the controller 100 may be configured to adjust the speed of the walk-behind lawn mower to 3 mph. Furthermore, the controller may additionally receive data from the user fitness device 250 that the historical average walking speed of the user is 2 mph in snow conditions. In cases, where the tool 10 is a snow thrower (i.e., a tool used in snow conditions), the controller 100 may be configured to adjust the speed of the snow thrower to 2 mph. Of course, it should be understood that the user may override or adjust the personalized drive speed via the application 322 or the informational unit 70.

As mentioned above, the data received from the user fitness device 250 may include average walking speed, heart rate, blood pressure, sweat volume, temperature, blood glucose levels, calories burned, UV exposure, oxygen content, or the like, or any combination thereof. Accordingly, any of these metric received by the controller 100 or the application server 340 may be used to adjust or configure the operational settings of the tool 10. In some cases, the operational settings of the tool 10 may be configured to never exceed the fitness ability of the user, as determined based on the data received from the user fitness device 250 or preset health or fitness thresholds. These thresholds may be set by the user via the informational unit 70 or the application 322 or may be thresholds recommended by various healthcare organizations (U.S. Federal Drug Administration or the like). For example, if the sweat volume or temperature of the user is detected as exceeding a predetermined limit, the controller 100 may be configured to decrease the operating speed of, power off the tool 10, recommend the user take a rest break, or the like in order to ensure well-being of the user (e.g., ensuring the user does not overheat, etc.). Furthermore, the controller 100 may be configured to take into account external parameters such as detected weather conditions, temperature, lot/lawn conditions, or the like when determining operational settings of the tool 10. These settings may be detected by the controller 100 or inputted as discussed herein.

Furthermore, in some example embodiments, the controller 100 may be configured to use the last received fitness data or metrics of the user to determine the initial settings of the tool 10 upon startup or powering on of the device. In other words, the last received fitness data or metrics of the user received by the controller may be predictive of initial startup settings of the next operation of the tool 10. In some cases, the controller 100 may be configured to average the health or fitness metrics of the user over a predetermined period of a time (e.g., a week, month, etc.) and use the average of the metrics to determine the initial settings of the tool 10 upon the startup of the tool 10.

In further example embodiments, the controller 100 may be configured to use the fitness data or metrics to calculate how long the remaining charge level of the battery-powered power source 14 will last at the detected fitness level of the user. In this regard, the controller 100 may be configured to use metrics such as the maximum or average walking speed of the user to determine how long the battery charge will last. This determination may be optionally communicated to the user (via application 322 or the information unit 70) such that the user has access to the remaining charge level of the battery pack 150 and can plan the use of the tool 10 accordingly. It should be understood that metrics that include determined maximums or averages (e.g., average or maximum walking speed) may be determined directly by the user fitness device 250 or by the controller 100 or the application server 340 based on data received by the user fitness device 250.

In some cases and as discussed above, the user via the application 322 or the information unit 70 may override or manually adjust or input any changes the controller 100 makes to the operation of the tool 10. For example, the user may manually increase or decrease an operating speed of the tool 10. Furthermore, the user may input lawn/lot size, ground condition, grass type, weather conditions, fitness goals, etc., and these conditions may be used to in determining the personalized settings of the tool 10 or otherwise configuring the tool 10 accordingly. Additionally, the controller may be configured to cause, either on the application 322 or the information unit 70, an alert or warning that notifies the user that a metric of the user fitness profile has been exceeded (e.g., blood pressure, temperature, etc.). The alert may give the user the option to override the alert or warning within a predetermined period of time (e.g., 30 seconds) in order to avoid a change in operational parameters of the tool 10 (e.g., shutdown of the tool 10).

In accordance with other example embodiments, the controller 100 may be configured to recommend settings of the tool 10 to ensure the tool 10 is being operated in a manner that ensures the most efficient and optimum operation of the tool 10. In this regard, based on the fitness data received by the controller 10, the tool 10 may be operated according to conditions that correspond to the fitness data of the user. However, these operating conditions may not necessarily correspond to operating conditions that will ensure optimal performance of the tool 10. Accordingly, the controller 100 may recommend operating conditions that will enable the tool 10 to operate at an optimal performance level. The user may then have the option to adjust the settings to correspond to optimal performance operating conditions rather than exclusively or periodically based on the fitness data or metrics.

It should also be understood that the user may have access to the data that is being communicated to the controller 100 or the application server 340. For example, the user may be notified (via the application 322 or the information unit 70) when the controller 100 changes operational parameters or when the controller 100 has recommendations. In this regard, the controller 100 may cause one or more alerts or reports to be displayed, via application 322, on the user fitness device or the information unit 70.

Furthermore, a manufacturer or retailer may have access to the data (e.g., via the server network 332) in order to enable the manufacturer or retailer to make recommendations regarding use of the tool 10 or if a different tool 10 will enable the user to achieve better performance and further optimize the time spent with the tool 10. The data may also be recorded or stored via the server network 332 so that the data may be transferred to a new tool 10 in the event the user replaces the tool 10.

Additionally, while embodiments described herein were generally described in relation to a single user of the tool 10, the capability of the system 310 may be particularly useful in applications that involve the management of a fleet of devices 110 used in a commercial setting. A manager of the fleet, for example, may then have the ability to monitor the health and safety of the users operating the tools 10 in the fleet and ensure each tool 10 of the fleet is being operated appropriately.

As can be appreciated from the example embodiments above, some embodiments may provide a controller 100 that may receive certain operational parameters from the tool 10 and certain fitness data from the user fitness device 250. The fitness data may be compared, by the controller 100, to the operational parameters of the tool 10 or other preset thresholds to determine personalized operating settings for the specific user. In order to determine the personalized operating settings of the user, different communication paradigms and analyses may be performed on the operational parameters and fitness data.

Figure 4:
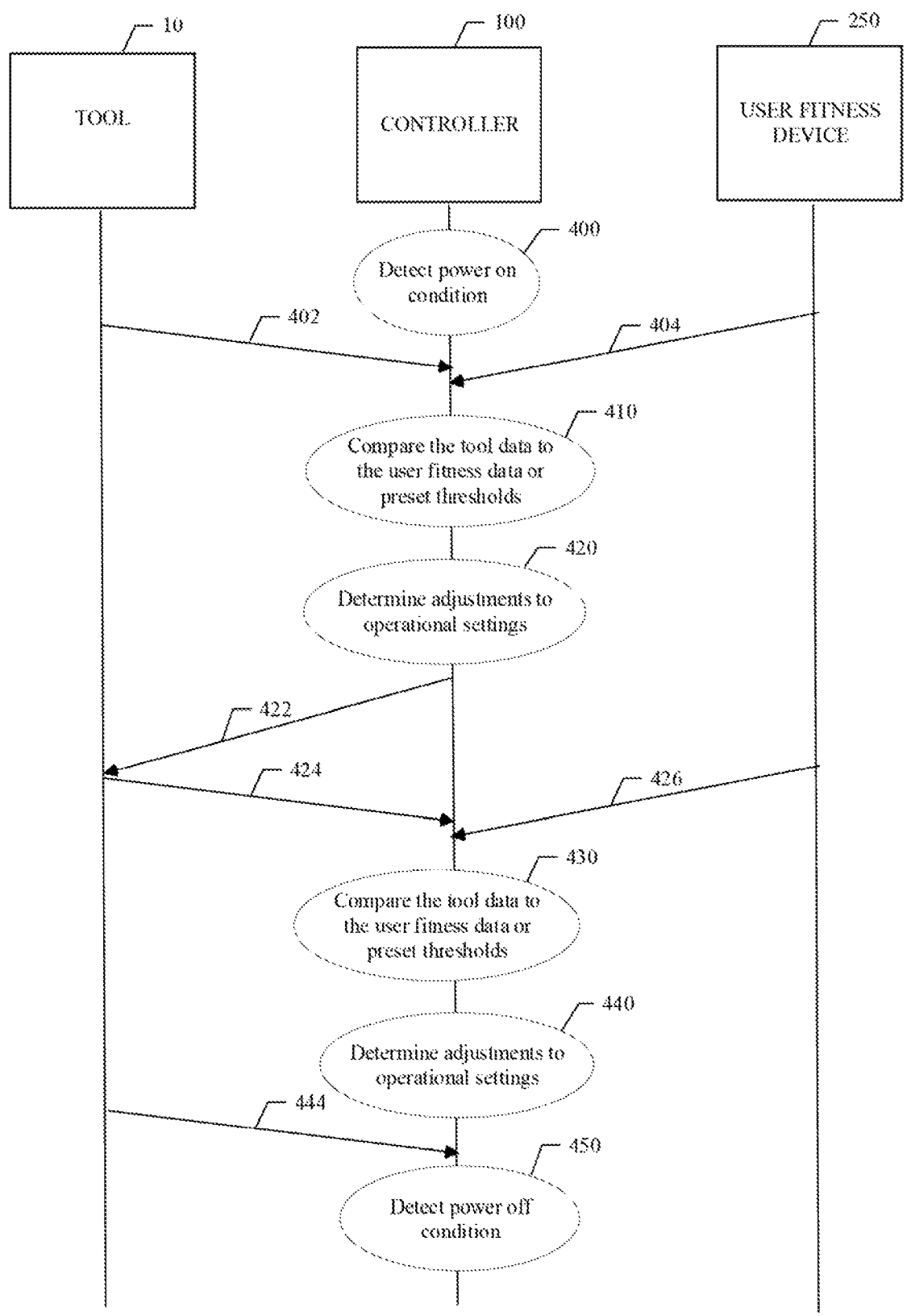
FIG. 4 illustrates a control flow diagram for personalizing operational settings of a device for a specific user according to an example embodiment.
Figure 5:
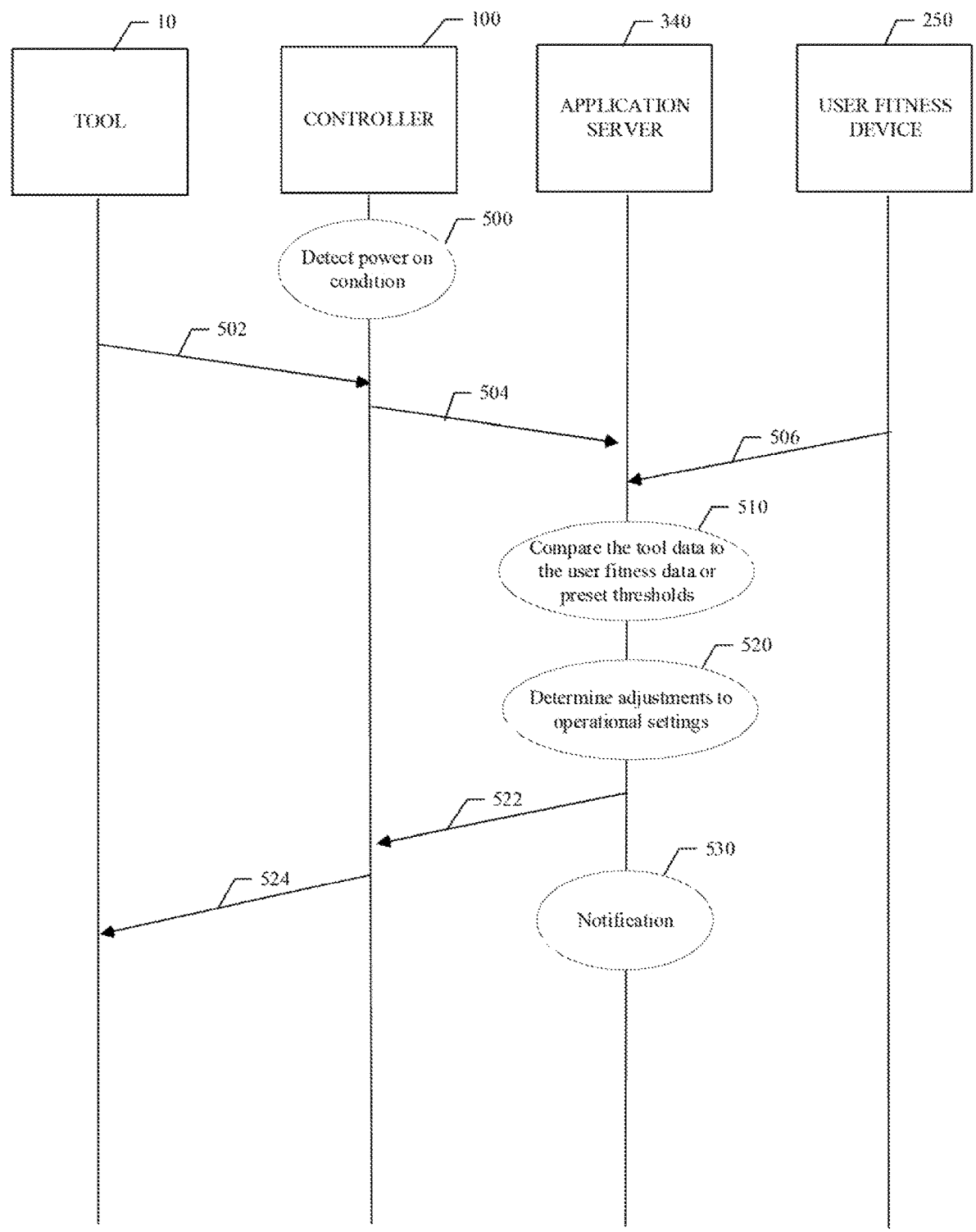
FIG. 5 illustrates a control flow diagram for personalizing operational settings of a device for a specific user according to a further example embodiment.
Figure 6:
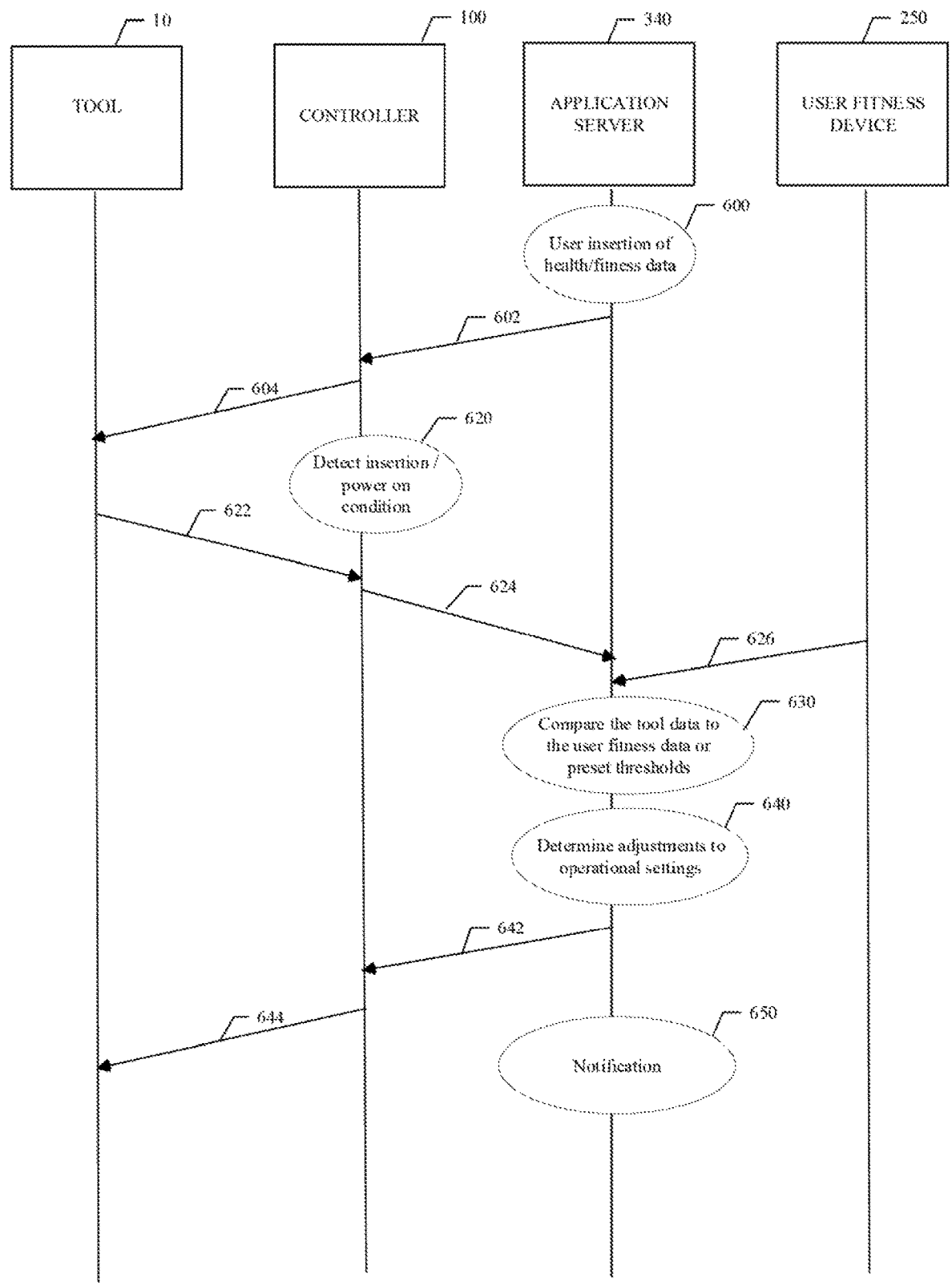
FIG. 6 illustrates a control flow diagram for personalizing operational settings of a device for a specific user according to an even further example embodiment.

FIGS. 4-6 illustrate various example control flow diagrams illustrating a series of communication operations associated with operation of the controller 100, tool 10, and user fitness device 250. As shown in FIG. 4, the controller 100 may initially detect a power on condition of the tool 10 (e.g., current draw above a predetermined threshold) at operation 400. Thereafter, operational parameters may be extracted from the tool 10 by the controller 100 at operation 402. User fitness data may be received from the user fitness device 250 by the controller 100 at operation 404. The operational parameters may be compared to the user fitness data or preset thresholds by the controller 100 at operation 410. Based on this comparison, the controller 100 may determine that adjustments are needed to the operational parameters (e.g., based on the stored user fitness profile, the controller 100 may determine that the mobility assembly 20 and the working assembly of the tool 10 needs to be adjusted to a lower speed to correspond to the average walking speed of the user) at operation 420. In some cases, when the mobility assembly speed is slowed the working assembly needs to be also slowed to ensure an optimal cutting operation by the tool 10.

At operation 422, the controller may cause the tool 10 (via the sensor network 60) to change the operational settings of the tool 10 accordingly. Even after the adjustment of operational settings of the tool 10, the controller 100 may continue to extract operational parameters from the tool 10 by the controller 100 at predetermined times at operation 424. User fitness data may also be continued to be periodically received from the user fitness device 250 by the controller 100 at operation 426. Of course, it should be understood that rather than periodically receiving data from the tool 10 and the user fitness device 250, the data may continually be received and monitored by the controller 100, for example, during operation of the tool 10. At operation 430, the controller 100 may again compare the operational parameters to the user fitness data or preset thresholds to ensure the tool 10 is operating in a manner to ensure optimum user health. If necessary, at operation 440, the controller 100 may again determine if adjustments are needed to the operational parameters. In this example, no further operational changes were communicated to the tool 10 by the controller 100. Further receipt of the operational parameters from the tool 10 was received by the controller 100 at operation 444. At operation 450, the controller 100 may detect a power off condition of the tool 10 (e.g., current draw below a predetermined threshold).

In the example of FIG. 5, the controller 100 may initially detect a power on condition of the tool 10 (e.g., current draw above a predetermined threshold) at operation 500. Thereafter, operational parameters may be extracted from the tool 10 by the controller 100 at operation 502. At operation 504, these operational parameters may be relayed to the application server 340. User fitness data may be received from the user fitness device 250 by the application server 340 at operation 506. The operational parameters may be compared to the user fitness data or preset thresholds by the application server 340 at operation 510. Based on this comparison, the application server 340 may determine that adjustments are needed to the operational parameters at operation 520. At operation 522, the application server 340 may relay any adjustments to the controller 100 at operation 522. At operation 524, the controller 100 may cause the tool 10 (via the sensor network 60) to change the operational settings of the tool 10 accordingly. At operation 530, the application server may provide a notification to the user (via the application 322) that settings of the tool 10 have been changed.

In the example of FIG. 6, the user may initially insert fitness data into the application 322 of the user fitness device 250 for transmission by the application server 340 in order to facilitate the personalization of initial settings of the tool 10 at operation 600. The application server 340 may provide this data to the controller at operation 602. At operation 604, the controller 100 may cause the tool 10 (via the sensor network 60) to change the operational settings of the tool 10 accordingly. Thereafter, the controller 100 may initially detect a power on condition of the tool 10 (e.g., current draw above a predetermined threshold) at operation 620. Operational parameters may be extracted from the tool 10 by the controller 100 at operation 622. At operation 624, these operational parameters may be relayed to the application server 340. User fitness data may be received from the user fitness device 250 by the application server 340 at operation 626. The operational parameters may be compared to the user fitness data or preset thresholds by the application server 340 at operation 630. Based on this comparison, the application server 340 may determine that adjustments are needed to the operational parameters at operation 640. At operation 642, the application server 340 may relay any adjustments to the controller 100. At operation 644, the controller 100 may cause the tool 10 (via the sensor network 60) to change the operational settings of the tool 10 accordingly. At operation 640, the application server may provide a notification to the user (via the application 322) that settings of the tool 10 have been changed.

Figure 7:
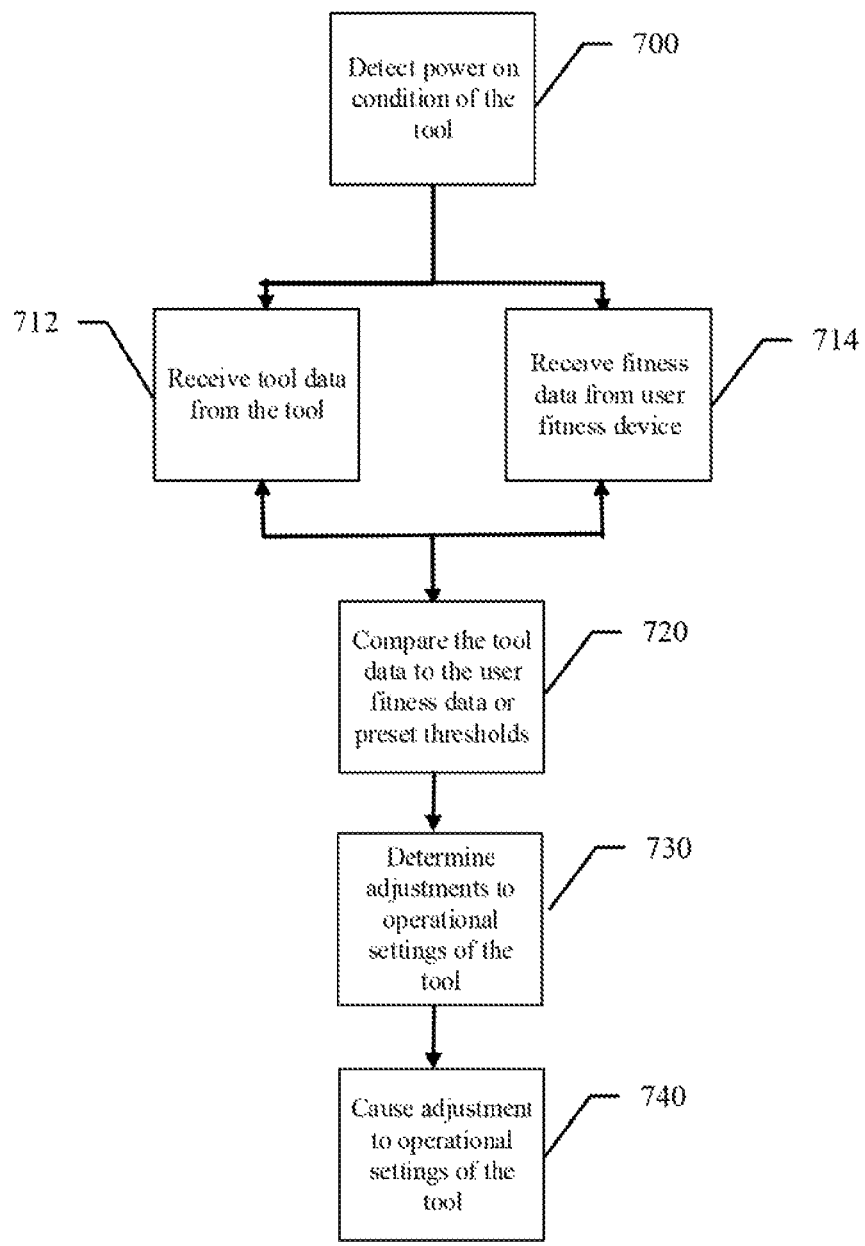
FIG. 7 illustrates a method for personalizing operational settings of a device for a specific user according to an example embodiment.

FIG. 7 is a flowchart of a method according to an example embodiment of the system 310. It will be understood that each block of the flowchart, and combinations of blocks in the flowchart, may be implemented by various means, such as hardware, firmware, the processor 212 or the processing circuitry 210 of the controller 100, as described in relation to FIG. 2 or similar processing circuitry of the application server 340.

The method may include, detecting a power or startup condition of the tool 10 at operation 700. The method may further include extracting operational parameters from the tool 10 at operation 712 and receiving fitness data of the user from the user fitness device 140 at operation 714. The operational parameters may include the battery status, energy efficiency, device speed, blade speed, blade height, or the like of the tool 10, and the fitness data may include average walking speed, heart rate, blood pressure, sweat volume, temperature, blood glucose levels, calories burned, UV exposure, oxygen content, or the like. These operational parameters may be compared to the fitness data of the user at operation 720. In some cases, the comparison may include establishing an initial user fitness profile based on data inputted from or sent via the user in association with, for example, an initial use of the tool 10, the data previously received from previous operations of the device (e.g., machine learned), or preset health thresholds received either from the user or based on recommendations from health organizations.

The user fitness profile may include a maximum and average walk speed of the user, a resting and active heart rate, recommended UV exposure, blood pressure, temperature and sweat volume guidelines, or the like. In this regard, the user fitness profile may be a static profile during use of the tool 10 that is set at a predetermined time (before or after an operation of the device) for use during the operation of the tool 10. However, it should be understood that the user fitness profile may change periodically—after each of use of the tool 10, for example, to account for new fitness data received—and used to compare to the tool data. In this regard, the user fitness profile and the tool data may be used as a benchmark against all received fitness data of the user received during user of the tool 10. For instance, the user fitness profile may be used to enable the user to achieve particular fitness goals or to ensure the safety of the user. The comparison of the received fitness data of the user to the sensor data and the user fitness profile may be used to monitor the work level of the user or to ensure control over various components of the tool 10 (e.g., working assembly or mobility assembly 20).

The method may also include determining adjustments to the operational parameters to ensure the operational settings of the tool 10 correspond to the user's fitness profile at operation 730 and causing the adjustments to the operational parameters of the tool 10 in accordance with the instructions received at operation 740. The determination of adjustments includes, for instance, that if the user fitness profile contains a maximum heart rate and data received from the user fitness device 250 indicates that user's detected rate is above this maximum heart rate, the controller 100 may cause a shut down or slowdown of the tool 10. The slowdown of the tool 10 may include a slowdown only to the mobility assembly 20. In some cases, any change to the mobility assembly 20 may also include a corresponding change to the working assembly or various other components of the tool 10. In some cases, in response to the receipt of data that indicates that the tool 10 has been in operation for 2.5 hours, which exceeds the recommend UV exposure of 2 hours as set forth in the user's fitness profile, the controller 100 may cause a shutdown of the tool 10. Of course, these examples should be understood to be in no way limiting to the capability of the controller 100 described herein.

Example embodiments therefore represent a controller for an outdoor power equipment tool. The controller may include processing circuitry operably coupled to a sensor network of the outdoor power equipment tool and in data communication with a network. The processing circuitry is configured to receive fitness data of a user from a fitness device via the network. The processing circuitry is further configured to receive sensor data from the sensor network, the sensor data corresponding to operational parameters of the outdoor power equipment tool. The processing circuitry is even further configured to compare the fitness data to the sensor data, and in response to the comparison of the fitness data to the sensor data, causing an adjustment to the operational parameters of the outdoor power equipment tool.

In some embodiments, additional optional structures or features may be included or the structures/features described above may be modified or augmented. Each of the additional features, structures, modifications, or augmentations may be practiced in combination with the structures/features above or in combination with each other. Thus, some, all or none of the additional features, structures, modifications, or augmentations may be utilized in some embodiments. Some example additional optional features, structures, modifications, or augmentations are described below, and may include, for example, that the comparison of the fitness data to the sensor data further includes comparing the fitness data to the sensor data and preset fitness thresholds, and in response to the comparison of the fitness data to the sensor data or preset fitness thresholds, causing the adjustment to the operational parameters. Alternatively or additionally, the comparison of the fitness data to the sensor data may further include comparing the fitness data to the sensor data and preset fitness thresholds, and in response to the comparison of the fitness data to the sensor data or preset fitness thresholds, causing the adjustment to the operational parameters. Alternatively or additionally, the comparison of the fitness data to the sensor data may further include comparing the fitness data to the sensor data and preset fitness thresholds, and in response to the comparison of the fitness data to the sensor data or preset fitness thresholds, causing the adjustment to the operational parameters. Alternatively or additionally, the preset fitness thresholds or the fitness data associated with a previous operation of the outdoor power equipment tool may be used to create a user fitness profile, the comparison of the fitness data to the sensor data and the preset fitness thresholds including comparing fitness data being currently received to the sensor data and the user fitness profile, and in response to the comparison of the fitness data currently being received to the sensor data or the user fitness profile, causing the adjustment to the operational parameters of the outdoor power equipment tool. Alternatively or additionally, the user fitness profile may remain static during operation of the outdoor power equipment tool. Alternatively or additionally, the user fitness profile may be updated before or after the operation of the outdoor power equipment tool based on the fitness data received during the previous operation of the outdoor power equipment tool. Alternatively or additionally, the processing circuitry may be configured to set initial operational parameters of the outdoor power equipment tool based on the user fitness profile. Alternatively or additionally, the preset fitness thresholds may be also based in part on recommendations from a healthcare organization. Alternatively or additionally, the operational parameters may include battery status, energy efficiency, device speed, blade speed, or blade height. Alternatively or additionally, the fitness data may include heart rate, blood pressure, sweat volume, temperature, blood glucose levels, calories burned, UV exposure, or oxygen content. Alternatively or additionally, the outdoor power equipment tool may be a walk behind lawn care device. Alternatively or additionally, the adjustment to the operational parameters may include adjusting a speed of a mobility assembly of the outdoor power equipment tool. Alternatively or additionally, adjusting the speed of the mobility assembly may cause a corresponding adjustment to a speed of the working assembly.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements or functions, it should be appreciated that different combinations of elements or functions may be provided by alternative embodiments without departing from the scope of the appended claims. In this regard, for example, different combinations of elements or functions than those explicitly described above are also contemplated as may be set forth in some of the appended claims. In cases where advantages, benefits or solutions to problems are described herein, it should be appreciated that such advantages, benefits or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. A controller for an outdoor power equipment tool, the controller comprising:
   processing circuitry operably coupled to a sensor network of the outdoor power equipment tool and in data communication with a network, wherein the processing circuitry is configured to:
   receive preset fitness thresholds from a user via the fitness device or an information unit of the outdoor power equipment tool;
   receive fitness data of a user from a fitness device via the network;
   receive sensor data from the sensor network, the sensor data corresponding to operational parameters of the outdoor power equipment tool;
   compare the fitness data to the sensor data and the preset fitness thresholds; and
   in response to the comparison of the fitness data to the sensor data and the preset fitness thresholds, cause an adjustment to the operational parameters of the outdoor power equipment tool.

2. The controller of claim 1, wherein the preset fitness thresholds or the fitness data associated with a previous operation of the outdoor power equipment tool are used to create a user fitness profile, wherein the comparison of the fitness data to the sensor data and the preset fitness thresholds comprises comparing fitness data currently being received to the sensor data and the user fitness profile, and wherein in response to the comparison of the fitness data currently being received to the sensor data or the user fitness profile, causing the adjustment to the operational parameters of the outdoor power equipment tool.

3. The controller of claim 2, wherein the user fitness profile remains static during operation of the outdoor power equipment tool.

4. The controller of claim 3, wherein the user fitness profile is updated before or after operation of the outdoor power equipment tool based on the fitness data received during a previous operation of the outdoor power equipment tool.

5. The controller of claim 2, wherein the processing circuitry is configured to set initial operational parameters of the outdoor power equipment tool based on the user fitness profile.

6. The controller of claim 1, wherein the preset fitness thresholds are also based in part on recommendations from a healthcare organization.

7. The controller of claim 1, wherein the operational parameters comprise battery status, energy efficiency, device speed, blade speed, or blade height.

8. The controller of claim 1, wherein the fitness data comprises heart rate, blood pressure, sweat volume, temperature, blood glucose levels, calories burned, UV exposure, or oxygen content.

9. The controller of claim 1, wherein the outdoor power equipment tool is a walk behind lawn care device.

10. The controller of claim 1, wherein the adjustment to the operational parameters comprises adjusting a speed of a mobility assembly of the outdoor power equipment tool.

11. The controller of claim 10, wherein adjusting the speed of the mobility assembly causes a corresponding adjustment to a speed of the working assembly.

12. A method for adjusting operational parameters of an outdoor power equipment tool, the method comprising:
   receiving preset fitness thresholds from a user via a fitness device or an information unit of the outdoor power equipment tool;
   receiving fitness data of a user from the fitness device via a network;
   receiving sensor data from a sensor network of the outdoor power equipment tool, the sensor data corresponding to operational parameters of the outdoor power equipment tool;
   comparing the fitness data to the sensor data and the preset fitness thresholds; and
   in response to the comparison of the fitness data to the sensor data and the preset fitness thresholds, causing an adjustment to the operational parameters of the outdoor power equipment tool.

13. The method of claim 12, wherein the method further comprises creating a user fitness profile based on preset fitness thresholds or the fitness data associated with a previous operation of the outdoor power equipment tool, and wherein the comparing of the fitness data to the sensor data and the preset fitness thresholds comprises comparing fitness data currently being received to the sensor data and the user fitness profile, and wherein in response to the comparison of the fitness data to the sensor data or the user fitness profile, causing the adjustment to the operational parameters of the outdoor power equipment tool.

14. The method of claim 13, wherein the user fitness profile remains static during operation of the outdoor power equipment tool, and
   wherein the method further comprises updating the user fitness profile before or after operation of the outdoor power equipment tool based on the fitness data received during a previous operation of the outdoor power equipment tool.

15. The method of claim 12, wherein the operational parameters comprise battery status, energy efficiency, device speed, blade speed, or blade height.

16. A system comprising:
   an outdoor power equipment tool comprising a sensor network and a controller; and
   a fitness device,
   wherein the controller comprises processing circuitry operably coupled to the sensor network of the outdoor power equipment tool and in data communication with a network,
   wherein the processing circuitry is configured to:
      receive preset fitness thresholds from a user via the fitness device or an information unit of the outdoor power equipment tool;
      receive fitness data of a user from the fitness device via the network;
      receive sensor data from the sensor network, the sensor data corresponding to operational parameters of the outdoor power equipment tool;
      compare the fitness data to the sensor data and the preset fitness thresholds; and
      in response to the comparison of the fitness data to the sensor data and the preset fitness thresholds, causing an adjustment to the operational parameters of the outdoor power equipment tool.

* * * * *